(12) United States Patent
Shenai-Khatkhate et al.

(10) Patent No.: US 8,962,893 B2
(45) Date of Patent: Feb. 24, 2015

(54) ORGANOMETALLIC COMPOUND PURIFICATION

(75) Inventors: Deodatta Vinayak Shenai-Khatkhate, Danvers, MA (US); Stephen J. Manzik, Hampstead, NH (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 130 days.

(21) Appl. No.: 13/596,050

(22) Filed: Aug. 28, 2012

(65) Prior Publication Data

US 2014/0061956 A1   Mar. 6, 2014

(51) Int. Cl.
*C07F 3/02*   (2006.01)
*C07F 17/00*   (2006.01)

(52) U.S. Cl.
CPC .. *C07F 3/02* (2013.01); *C07F 17/00* (2013.01)
USPC .......................................... 568/456; 568/455

(58) Field of Classification Search
USPC ................................. 568/455, 456
See application file for complete search history.

(56) References Cited

U.S. PATENT DOCUMENTS

| | | | |
|---|---|---|---|
| 5,302,733 A | 4/1994 | Diefenbach et al. | |
| 5,569,746 A | 10/1996 | Lee et al. | |
| 5,648,308 A | 7/1997 | Lee et al. | |
| 5,770,752 A | 6/1998 | Kaufmann et al. | |
| 7,223,878 B2 | 5/2007 | Schulte et al. | |
| 8,313,807 B2 * | 11/2012 | Norman et al. | 427/255.36 |
| 2006/0226075 A1 | 10/2006 | Shenai-Khatkhate et al. | |
| 2011/0120875 A1 * | 5/2011 | Norman | 205/80 |

FOREIGN PATENT DOCUMENTS

| | | |
|---|---|---|
| CA | 2328728 | 3/1999 |
| JP | 2007-254408 | 4/2007 |
| WO | WO 97/21717 | 6/1997 |

OTHER PUBLICATIONS

Eisch et al, "Facile magnesiation of carbon bronsted acids with electrophilic, donor-free alkylmagnesium compounds", Journal of Organometallic Chemistry, 1985, pp. C27-C31, vol. 296.

Lucht et al, "Polydentata amine and ether solvates of lithium hexamethyldisilazide (LiHMDS): relationship with ligand structure, relative salvation energy and aggregation state"; J. Am. Chem. Soc. 1996; vol. 118; pp. 10707-10718.

Xia, et al, "Synthesis, structure, and properties of magnesium complexes containing cyclopentadienyl and admidinate ligand sets"; Journal of Organometallic Chemistry; 2003, vol. 682; pp. 224-232.

Xia, et al, "Synthesis, structure, and properties of maganesocene amine adducts. Structural distortions arising from N-H•••$C_5H_5$ hydrogen bonding and molecular orbital calculations thereof"; Organometallics 2003; vol. 22; pp. 4060-4069.

* cited by examiner

*Primary Examiner* — Sudhakar Katakam
*Assistant Examiner* — Pancham Bakshi
(74) *Attorney, Agent, or Firm* — S. Matthew Cairns

(57) ABSTRACT

Methods of purifying crude cyclopentadienyl magnesium compounds using a scavenging agent are provided. The purified cyclopentadienyl magnesium compounds have very low levels of metallic impurities.

17 Claims, No Drawings

ORGANOMETALLIC COMPOUND PURIFICATION

This application claims the benefit of priority under 35 U.S.C. §119(e) to U.S. Provisional Application No. 61/527,985, filed Aug. 26, 2011, the entire contents of which application are incorporated herein by reference.

The present invention relates to the field of metal-containing compounds and particularly to the field of purifying metal-containing compounds.

Metal-containing compounds are used in a variety of applications, such as catalysts and sources for growing metal films. One use of such compounds is in the manufacture of electronic devices such as semiconductors. Many semi-conducting materials are manufactured using well-established deposition technologies that employ ultrapure metalorganic (organometallic) compounds, for example, metalorganic vapor phase epitaxy, metalorganic molecular beam epitaxy, metalorganic chemical vapor deposition and atomic layer deposition. To be useful in these processes the organometallic compounds must be free from contaminants and/or deleterious impurities, such as metallic impurities and organic impurities. If not removed, such impurities present in the organometallic sources can cause adverse effects on the electronic and/or optoelectronic properties of electronic devices.

Crude organometallic compounds typically contain various impurities resulting from reaction by-products, impurities in starting materials, residual solvent, or any combination of these. Such impurities are often very difficult to remove from the desired organometallic compound. Various methods have been used to purify such crude organometallic compounds, such as distillation, sublimation, and crystallization.

U.S. Pat. No. 5,770,752 discloses a method of removing organometallic byproducts from metallocene product mixtures used as catalysts, comprising contacting the metallocene product mixture with a polar extractant composition, where the metallocene comprises a main group transition metal from group III, IV, V or VI. The polar extractant composition comprises a polar solvent, such as alcohols, ethers, carboxylic acids, carboxylic acid esters, carboxylic acid amides, amines, alkyl halides and aromatic hydrocarbons. Many of these polar solvents are known to react with other metallocene compounds, such as bis(cyclopentadienyl)magnesium. Also, this patent fails to recognize the problem of residual solvent contamination in the use of organometallic compounds in the deposition of thin films for use in electronic devices.

Japanese patent application 2007-254408 A discloses a method of preparing high purity bis(cyclopentadienyl)magnesium ("Cp$_2$Mg") by reacting dialkylmagnesium with slightly more than 2 mole equivalents of cyclopentadiene in the presence of a tri(C$_6$-C$_{12}$)alkylamine, followed by sublimation of the reaction mixture under reduced pressure to provide high purity Cp$_2$Mg. While this method may produce Cp$_2$Mg having low levels of certain metal impurities, it introduces unacceptable levels of amine impurities into the Cp$_2$Mg, which can lead to carbon incorporation in vapor deposited films.

There remains a need to provide cyclopentadienyl magnesium compounds in very high purity, with very low levels of impurities.

The present invention provides a method of purifying a cyclopentadienyl magnesium compound comprising the steps of: providing a crude cyclopentadienyl magnesium compound; contacting the crude cyclopentadienyl magnesium compound with a scavenging agent comprising two or more tertiary amine groups; and separating purified cyclopentadienyl magnesium compound from the scavenging agent.

The present invention also provides cyclopentadienyl magnesium compounds having ≤0.5 ppm of total detectable metals. Preferably, the cyclopentadienyl magnesium compound is bis(cyclopentadienyl)magnesium magnesium, in which each cyclopentadienyl ring may be optionally substituted with one or more (C$_1$-C$_4$)alkyl groups. More preferably, the cyclopentadienyl magnesium compound contains ≤0.3 ppm of total detectable metals.

The articles "a" and "an" refer to the singular and the plural. "Alkyl" includes straight chain, branched and cyclic alkyl. "Halogen" refers to fluorine, chlorine, bromine and iodine. The following abbreviations shall have the following meanings: ppm=parts per million; g=grams; kg=kilograms; mL=milliliters; Pa=Pascals; and ° C.=degrees Celsius. Unless otherwise noted, all amounts are percentages by weight and all ratios are molar ratios. All numerical ranges are inclusive and combinable in any order except where it is clear that such numerical ranges are constrained to add up to 100%.

The present invention provides a method of purifying a cyclopentadienyl magnesium compound comprising contacting a crude cyclopentadienyl compound with a scavenging agent comprising two or more tertiary amine groups. The scavenging agent comprising two or more tertiary amine groups is selected such that it does not react with the cyclopentadienyl magnesium compound. The crude cyclopentadienyl magnesium compound may contain one or more impurities chosen from unreacted starting materials, reaction by-products, and metallic impurities. The metallic impurities may include organometallic impurities and inorganic salts. Metallic impurities may be present in one or more of the starting materials used to make the cyclopentadienyl magnesium compounds. The presence of such impurities in the cyclopentadienyl magnesium compounds may be deleterious in many applications, such as in electronics applications, where even very low levels of impurities may adversely affect the electrical properties of thin films.

Suitable cyclopentadienyl magnesium compounds have either two cyclopentadienyl rings, which may be substituted or unsubstituted, or one amidinate group and one cyclopentadienyl ring, which may be substituted or unsubstituted. As used herein, an "amidinate" group also includes a "formidinate" group and a "guanidinate" group. Typically, the cyclopentadienyl rings may be substituted with one or more (C$_1$-C$_4$)alkyl groups. Preferably, the cyclopentadienyl magnesium compounds have the formula (amd)$_n$Mg(C$_5$R$_5$)$_{2-n}$, wherein: amd=amidinate; each R is independently chosen from H, and (C$_1$-C$_4$)alkyl; and n=0 or 1. Each R is preferably chosen from H and (C$_1$-C$_3$)alkyl, and more preferably from H, methyl and ethyl, and even more preferably from H and methyl. Preferably, n=0. In the above formula, C$_5$R$_5$ refers to a cyclopentadienyl ring. It is particularly preferred that n=0 and R=H or (C$_1$-C$_3$)alkyl, more preferred that n=0 and R=H, methyl or ethyl; and even more preferred that n=0 and R=H or methyl. Preferably, the amidinate group (amd) has the formula:

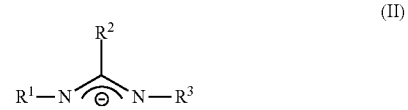

(II)

wherein: $R^1$ and $R^3$ are independently chosen from H, ($C_1$-$C_6$)alkyl, and ($C_6$-$C_{10}$)aryl; $R^2$ is chosen from H, $NR^4R^5$, ($C_1$-$C_6$)alkyl, and ($C_6$-$C_{10}$)aryl; and $R^4$ and $R^5$ are independently chosen from ($C_1$-$C_6$)alkyl, and ($C_6$-$C_{10}$)aryl. When $R^2$=H, the amd group is a formidinate group, and when $R^2$=$NR^4R^5$, the amd group is a guanidinate group. It is preferred that $R^1$ and $R^3$ are independently chosen from H, ($C_1$-$C_4$)alkyl, and ($C_6$-$C_{10}$)aryl, and more preferably from H, ($C_1$-$C_4$)alkyl, and phenyl. $R^2$ is preferably chosen from H, $NR^4R^5$, ($C_1$-$C_4$)alkyl, and ($C_6$-$C_{10}$)aryl, and more preferably from H, $NR^4R^5$ and ($C_1$-$C_4$)alkyl. It is preferred that $R^4$ and $R^5$ are independently chosen from ($C_1$-$C_6$)alkyl, more preferably from ($C_1$-$C_4$)alkyl, and even more preferably from ($C_1$-$C_3$)alkyl. Exemplary ($C_6$-$C_{10}$)aryl groups include, without limitation, phenyl, tolyl, xylyl, ethylphenyl, trimethylphenyl, diethylphenyl, 1,2,3,4-tetrahydronaphthenyl, and indenyl.

Preferred cyclopentadienyl magnesium compounds containing two cyclopentadienyl rings are: bis(cyclopentadienyl) magnesium; bis(methylcyclopentadienyl)magnesium; bis-(ethyl-cyclopentadienyl)magnesium; bis(propylcyclopentadienyl)magnesium; bis(iso-propyl-cyclopentadienyl)magnesium; bis(n-butylcyclopentadienyl) magnesium; and bis-(pentamethyl-cyclopentadienyl) magnesium. Particularly preferred cyclopentadienyl magnesium compounds are: bis(cyclopentadienyl)magnesium; bis(methylcyclopentadienyl)magnesium; and bis-(pentamethylcyclopentadienyl)magnesium; and more preferably bis(cyclopentadienyl)-magnesium and bis (pentamethylcyclopentadienyl)magnesium.

The cyclopentadienyl magnesium compounds useful in the present invention are commercially available from various sources or may be prepared by procedures known in the literature. For example, cyclopentadienyl magnesium compounds having two cyclopentadienyl rings may be prepared according to the procedure of Eisch et al., *J. Organomet. Chem.*, 1985, vol. 296, pp C27-C31. Cyclopentadienyl magnesium compounds having one cyclopentadienyl ring and an amidinate group may be prepared according to the procedure of Xia et al., *J. Organomet. Chem.*, 2003, vol. 682, pp 224-232.

Scavenging agents (or scavengers) useful in the present invention have two or more tertiary amine groups. Mixtures of scavenging agents may be used. Such scavenging agents are aprotic, that is, they do not contain a hydrogen bonded to an electron donating atom, such as oxygen, nitrogen or sulfur. It is preferred that cyclopentadienyl magnesium compound be insoluble in, or only sparingly soluble in, the scavenging agent. The tertiary amine groups in the scavenging agents may be cyclic or acyclic. Suitable scavenging agents have from 2 to 10 tertiary amine groups. Preferably, the scavenging agents have from 2 to 6 tertiary amine groups, more preferably from 2 to 4 tertiary amine groups and even more preferably from 2 to 3 tertiary amine groups. Preferably, the scavenging agent is composed of a hydrocarbon moiety having two or more tertiary amine groups. Such hydrocarbon moiety may be a cyclic or acyclic, and aromatic or non-aromatic. Preferably, the scavenging agent has the formula:

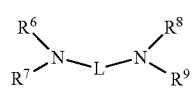

(III)

wherein: each of $R^6$, $R^7$, $R^8$, $R^9$ and $R^{10}$ are independently chosen from ($C_1$-$C_6$)alkyl, ($C_6$-$C_{10}$)aryl, and ($C_1$-$C_6$)alkyl ($C_6$-$C_{10}$)aryl; each of $R^6$ and $R^7$, and $R^8$ and $R^9$, may be taken together along with the nitrogen to which they are attached to form a 5- to 8-membered heterocyclic ring; $R^6$ and $R^8$ may be taken together along with the nitrogens to which they are attached to form a 5- to 8-membered heterocyclic ring; L=$(CH_2)_x(CH_2NR^{10}CH_2)_y(CH_2)_z$ or ($C_5$-$C_6$)cycloalkylene; x=0-10; y=0-4; and z=0 or 1; wherein x+y+z≥1. Preferably, each of $R^6$, $R^7$, $R^8$, $R^9$ and $R^{10}$ are independently chosen from ($C_1$-$C_4$)alkyl and ($C_6$-$C_{10}$)aryl, more preferably ($C_1$-$C_4$) alkyl, and most preferably ($C_1$-$C_2$)alkyl. When $R^6$ and $R^7$, or $R^8$ and $R^9$, are taken together along with the nitrogen to which they are attached to form a heterocyclic ring, it is preferred that they form a pyrrolidine (5-membered) or piperidine (6-membered) ring. It is preferred that x=1-6, more preferably 1-5, and even more preferably 1-4. It is preferred that y=0-2, and more preferably 0-1. When y>0, it is preferred that z=1. When y=0, it is preferred that z=0.

Preferred scavenging agents include: N,N,N',N'-tetramethylethylenediamine ("TMEDA"); N,N,N',N'-tetramethylmethylenediamine ("TMMDA"); N,N,N',N'-tetramethylpropylenediamine ("TMPDA"); N,N,N',N'-tetramethylbutylenediamine ("TBEDA"); N,N,N',N'-tetramethylcyclohexyldiamine ("TMCDA"); N,N,N',N'-tetraethylethylenediamine ("TEEDA"); N,N,N',N',N"-pentamethyldiethylenetriamine ("PMDETA"); 1,1,4,7,10,10-hexamethyltriethylenetetramine ("HMTETA"); 1,2-di(pyrrolidin-1-yl)ethane; 1,2-di(piperidin-1-yl)ethane; N,N'-dimethylpiperazine; 1,4,7-trimethyl-1,4,7-triazonane; and 1,3,5-trimethyl-1,3,5-triazinane. It is more preferred that the scavenging agent is chosen from N,N,N',N'-tetramethylethylenediamine; N,N,N',N'-tetramethylmethylenediamine; N,N,N',N'-tetramethyl-propylenediamine; N,N,N',N'-tetramethylbutylenediamine; N,N,N',N'-tetramethyl-cyclohexyldiamine; N,N,N',N'-tetraethylethylenediamine; N,N,N',N',N"-pentamethyl-diethylenetriamine; and 1,1,4,7,10,10-hexamethyltriethylenetetramine. Even more preferred are N,N,N',N'-tetramethylethylenediamine; N,N,N',N'-tetramethylpropylenediamine; N,N,N',N'-tetramethylbutylenediamine; N,N,N',N'-tetraethylethylenediamine; and N,N,N',N',N"-pentamethyldiethylenetriamine.

Suitable scavenging agents are generally commercially available from a variety of sources, or may be prepared by literature methods, such as in Lucht et al, *J. Am. Chem. Soc.*, 118 (1996) pp 10707-10718. The scavenging agents may be solids or liquids, and preferably are liquids.

Impurities, especially metallic impurities, are removed form the cyclopentadienyl magnesium compounds by contacting the cyclopentadienyl magnesium compounds with one or more of the above described scavenging agents. Such contacting step may be in the form of a recrystallization step, an extraction step, a washing step, or a combination of these steps. Preferably, the contacting step is a recrystallization step, an extraction step, or a combination thereof, and more preferably, the contacting step is an extraction step. When an extraction step or a washing step is used, the scavenging agent is selected such that the cyclopentadienyl magnesium compound is insoluble or sparingly soluble in it, and preferably insoluble in it.

The crude cyclopentadienyl magnesium compound is contacted with the one or more scavenging agents for a period of time sufficient to reduce the level of impurities. The amount of scavenging agent used is well within the ability of those skilled in the art. Preferably, the crude cyclopentadienyl magnesium compound and the one or more scavenging agents are contacted for a period of time sufficient to provide purified cyclopentadienyl magnesium compound substantially free of metallic impurities, that is, ≤0.5 ppm of total detectable metals. The exact contact time will vary with the particular cyclopentadienyl magnesium compound, the level of impurities, the particular impurities to be removed, the particular scavenging agent selected, and the particular contacting step chosen, amount and choice of organic solvent used, if any. Typical contact times are from 1 minute to 24 hours. Preferably contact times are from 1 minute to 12 hours, more preferably from 5 minutes to 12 hours, and even more preferably from 5 minutes to 10 hours.

Optionally, the contacting step is performed in the presence of an organic solvent. It is preferred that an organic solvent is present during the contacting step. A wide variety of organic solvents may be used, provided that the solvent does not react with or otherwise destabilize the cyclopentadienyl magnesium compound, and that the solvent is liquid at the temperature of use. Preferred organic solvents include, but are not limited to, hydrocarbons and ethers. Suitable hydrocarbons have from 5 to 35 carbon atoms, and may be aliphatic, cyclic or aromatic. Exemplary hydrocarbon organic solvents include: ($C_5$-$C_{16}$)alkanes such as pentane, hexane, heptane, octane, nonane, decane, dodecane, hexadecane; ($C_5$-$C_{16}$)cycloalkanes such as cyclopentane, cyclohexane, methylcyclohexane, cyclooctane, and decahydronaphthalene; linear alkyl benzenes; squalane; and ($C_6$-$C_{20}$)aromatic hydrocarbons, such as benzene, toluene, xylene, tetrahydronaphthalene, mesitylene, ethylbenzene, and chlorobenzene. Exemplary ethers include, without limitation, diethylether, tetrahydrofuran, 1,4-dioxane, glyme, ethylglyme, diglyme, ethyldiglyme, butyldiglyme, triglyme, and tetraglyme. It is preferred that the cyclopentadienyl magnesium compound be insoluble in, or only sparingly soluble in, any organic solvent used.

The particular amount of optional organic solvent used is not critical. The amount of optional organic solvent used depends upon the particular contacting step chosen, whether the scavenging agent or the crude cyclopentadienyl magnesium compound is a liquid, and the solubility of the crude cyclopentadienyl magnesium compound in the scavenging agent. The selection of the particular amount of organic solvent is well within the ability of those skilled in the art. When the scavenging agent is a liquid under the conditions of use, it may be used with or without an organic solvent in the present process. For example, if the crude cyclopentadienyl magnesium compound is sufficiently soluble in the liquid scavenging agent, then such scavenging agent may be used to recrystallize the cyclopentadienyl magnesium compound, removing impurities during the recrystallization step. Alternatively, if the cyclopentadienyl magnesium compound is insoluble or sparingly soluble in the liquid scavenging agent, such scavenging agent may be used in an extraction step to remove impurities. When the cyclopentadienyl magnesium compound to be purified is a liquid, such as bis(methylcyclopentadienyl)magnesium or bis(pentamethylcyclopentadienyl)magnesium, a solid or liquid scavenging agent may be used, either with or without the optional organic solvent.

When an organic solvent is used during the contacting step, the scavenging agent is typically present an amount of 0.5 to 90% by weight ("wt %"), based on the weight of the organic solvent. Preferably, the scavenging agent is present in an amount of 0.5 to 75 wt %, more preferably from 1 to 50 wt %, yet more preferably from 2 to 50 wt %, and still more preferably from 5 to 50 wt %.

Typically, the crude cyclopentadienyl magnesium compound, one or more scavenging agents, and optional organic solvent are added to a suitable vessel. Preferably, a slurry or suspension of the crude cyclopentadienyl magnesium compound is obtained. Such slurry or suspension is agitated, typically with a mechanical stirrer. Optionally, the vessel may be heated, and preferably the vessel is heated. The crude cyclopentadienyl magnesium compound is then contacted with the one or more scavenging agents for a period of time sufficient to reduce the level of impurities. Preferably, the crude cyclopentadienyl magnesium compound and the one or more scavenging agents are contacted for a period of time sufficient to provide purified cyclopentadienyl magnesium compound substantially free of metallic impurities, that is, ≤0.5 ppm of total detectable metals, and preferably ≤0.3 ppm. The exact contact time will vary with the particular cyclopentadienyl magnesium compound, the level of impurities, the particular impurities to be removed, the particular scavenging agent selected, and the amount and choice of organic solvent used, if any. Typical contact times are from 1 minute to 24 hours. Preferably contact times are from 1 minute to 12 hours, more preferably from 5 minutes to 12 hours, and even more preferably from 5 minutes to 10 hours.

Following contact with the scavenging agent, the purified cyclopentadienyl magnesium compound is then separated from the scavenging agent and any organic solvent used. Such separation may be accomplished by any suitable means, such as crystallization, filtration, sublimation and decantation. It is preferred that the purified cyclopentadienyl magnesium compound is separated form the scavenging agent by filtration or decantation. For example, if the cyclopentadienyl magnesium compound is soluble in the scavenging agent or organic solvent used, then purified cyclopentadienyl magnesium compound may be obtained by crystallization. If the cyclopentadienyl magnesium compound is insoluble or sparingly soluble in the scavenging agent or organic solvent used, purified cyclopentadienyl magnesium compound may be obtained by sublimation, filtration, or decantation, and preferably by filtration, or decantation.

The cyclopentadienyl magnesium compound obtained after separation from the scavenging agent is purified as compared with the starting crude cyclopentadienyl magnesium compound. Preferably, the purified cyclopentadienyl magnesium compound has ≤0.5 ppm of total detectable metals. More preferably, the cyclopentadienyl magnesium compound contains ≤0.3 ppm of total detectable metals, and yet more preferably contains ≤0.3 ppm of detectable metals and is free of scavenging agent.

EXAMPLE 1

$Cp_2Mg$ was prepared according to the method Eisch et al., *J. Organomet. Chem.*, 1985, vol. 296, pp C27-C31, and was purified by sublimation at reduced pressure (<13 Pa). Analysis of the purified $Cp_2Mg$ by inductively coupled plasma mass spectrometry ("ICP-MS") showed the presence of various deleterious impurities: Al (34.3 ppm); Fe (0.5 ppm); and Si (24.6 µm).

EXAMPLE 2

$Cp_2Mg$ (50 g, 0.324 moles) from Example 1 was suspended in degassed heptane (250 mL) in a 500 mL flask equipped with a mechanical stirrer and a condenser. N,N,N',N'-Tetramethylethylenediamine ("TMEDA") (1.9 g, 0.0162 moles) was then added to the suspension with constant stirring, while being maintained at room temperature. The mixture was next heated to about 110° C. for 2 hours. The $Cp_2Mg$ crystallized upon cooling to room temperature. The heptane layer was then decanted from the $Cp_2Mg$, and discarded. The white, crystalline $Cp_2Mg$ product was then washed with heptane (100 mL) and dried under vacuum (ca. 11 Pa) to remove all volatile impurities. The Cp$_2$Mg was then sublimed at reduced pressure (ca. 12 Pa) at 50° C. to provide purified Cp$_2$Mg. The purified Cp$_2$Mg was analyzed by ICP-MS and the amounts of Al, Fe and Si were found to be below the limit of detection (<0.1 ppm). Analysis of the purified Cp$_2$Mg by $^1$H FT-NMR showed no detectable level (<1 ppm) of any organic impurities, including residual TMEDA.

EXAMPLE 3

Three lots of Cp$_2$Mg, each made according to Example 1, were analyzed by ICP-MS to determine the level of Al and Si. These results are reported in the Table below.

| Cp$_2$Mg Lot No. | Al (ppm) | Si (ppm) |
| --- | --- | --- |
| 1 | 34.3 | 24.6 |
| 2 | 8 | 9 |
| 3 | 4 | 10 |

Cp$_2$Mg (2.6 kg, 16.9 moles) from lots 1 (1.07 kg), 2 (1.2 kg) and 3 (0.4 kg) was suspended in degassed heptane (ca. 13 L) in a 22 L flask equipped with a mechanical stirrer and a condenser. TMEDA (100 g, 0.85 moles) was then added to the suspension with constant stirring, while being maintained at room temperature. The mixture was next heated to reflux about 105° C. for 4 hours. The Cp$_2$Mg crystallized upon cooling to room temperature. The heptane layer was then decanted from the Cp$_2$Mg, and discarded. The white, crystalline Cp$_2$Mg product was then washed with heptane (2 L) and dried under vacuum (ca. 13 Pa) to remove all volatile impurities. The Cp$_2$Mg was then sublimed at reduced pressure (ca. 12 Pa) at 50° C. to provide purified Cp$_2$Mg. The purified Cp$_2$Mg was analyzed by ICP-MS and the amounts of Al and Si were each found to be 0.7 ppm. Analysis of the purified Cp$_2$Mg by $^1$H FT-NMR showed no detectable level (<1 ppm) of any organic impurities, including residual TMEDA.

EXAMPLE 4

The procedure of Example 2 is repeated except that the TMEDA is replaced with N,N,N',N',N''-pentamethyldiethylenetriamine

EXAMPLE 5

The procedure of Example 2 is repeated except that Cp$_2$Mg is replaced with bis(pentamethylcyclopentadienyl)magnesium.

EXAMPLE 6

The procedure of Example 4 is repeated except that the Cp$_2$Mg is replaced with bis(pentamethylcyclopentadienyl)magnesium.

EXAMPLE 7

The procedure of Example 2 is repeated except that the TMEDA is replaced with N,N,N',N'-tetramethylpropylenediamine.

EXAMPLE 8

The procedure of Example 7 is repeated except that the Cp$_2$Mg is replaced with bis(methylcyclopentadienyl)magnesium.

EXAMPLE 9

The procedure of Example 2 is repeated except that the Cp$_2$Mg is replaced with [CpMg($\eta^2$-t-BuC(N(2,6-i-Pr$_2$C$_6$H$_3$))$_2$] and the heptane is replaced with hexane, where "Cp"=cyclopentadienyl; "t-Bu"=tertiary-butyl; and "i-Pr"=iso-propyl.

Comparative Example 1

Cp$_2$Mg (50 g, 0.324 moles) from Example 1 was suspended in degassed heptane (250 mL) in a 500 mL flask equipped with a mechanical stirrer and a condenser. Tri-(n-hexyl)amine ("THA") (9 g, 0.0324 moles) was then added to the suspension with constant stirring, while being maintained at room temperature. The mixture was next heated to about 110° C. for 2 hours. The Cp$_2$Mg crystallized upon cooling to room temperature. The heptane layer was then decanted from the Cp$_2$Mg, and discarded. The white, crystalline Cp$_2$Mg product was then washed with heptane (100 mL) and dried under vacuum (ca. 11 Pa) to remove all volatile impurities. The Cp$_2$Mg was then sublimed at reduced pressure (ca. 12 Pa) at 50° C. to provide purified Cp$_2$Mg. The purified Cp$_2$Mg was analyzed by ICP-MS and the amount of Al was found to be 0.2 ppm, and the amounts of Fe and Si were found to be below the limit of detection (<0.1 ppm). Analysis of the purified Cp$_2$Mg by $^1$H FT-NMR showed significant levels (ca. 1400 ppm) of residual THA (detection limit of <1 ppm).

Comparative Example 2

Cp$_2$Mg (50 g, 0.324 moles) from Example 1 was suspended in degassed heptane (250 mL) in a 500 mL flask equipped with a mechanical stirrer and a condenser. Triethylamine ("TEA") (1.7 g, 0.0162 moles) was then added to the suspension with constant stirring, while being maintained at room temperature. The mixture was next heated to about 110° C. for 2 hours. The Cp$_2$Mg crystallized upon cooling to room temperature. The heptane layer was then decanted from the Cp$_2$Mg, and discarded. The white, crystalline Cp$_2$Mg product was then washed with heptane (100 mL) and dried under vacuum (ca. 11 Pa) to remove all volatile impurities. The Cp$_2$Mg was then sublimed at reduced pressure (ca. 12 Pa) at 50° C. to provide purified Cp$_2$Mg. The purified Cp$_2$Mg was analyzed by ICP-MS and the amount of Al was found to be 1 ppm, the amount of Si was found to be 0.6 ppm, and the amount of Fe was found to be below the limit of detection (<0.1 ppm). Analysis of the purified Cp$_2$Mg by $^1$H FT-NMR showed no detectable level (<1 ppm) of any organic impurities, including residual TEA.

What is claimed is:

1. A method of removing metallic impurities from a cyclopentadienyl magnesium compound comprising the steps of: providing a crude cyclopentadienyl magnesium compound; contacting the crude cyclopentadienyl magnesium compound with a scavenging agent comprising two or more tertiary amine groups to purify the cyclopentadienyl magnesium compound; and separating the purified cyclopentadienyl magnesium compound from the scavenging agent; wherein the scavenging agent is aprotic.

2. The method of claim 1 wherein the cyclopentadienyl magnesium compound has the formula: (amd)$_n$Mg(C$_5$R$_5$)$_{2-n}$, wherein: amd=amidinate; each R is independently chosen from H, and (C$_1$-C$_4$)alkyl; and n=0 or 1.

3. The method of claim 2 wherein the amd group has the formula:

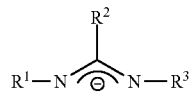
(II)

wherein: $R^1$ and $R^3$ are independently chosen from H, $(C_1\text{-}C_6)$alkyl, and $(C_6\text{-}C_{10})$aryl; $R^2$ is chosen from H, $NR^4R^5$, $(C_1\text{-}C_6)$alkyl, and $(C_6\text{-}C_{10})$aryl; and $R^4$ and $R^5$ are independently chosen from $(C_1\text{-}C_6)$alkyl, and $(C_6\text{-}C_{10})$aryl.

4. The method of claim 1 wherein the cyclopentadienyl magnesium compound is chosen from dicyclopentadienyl magnesium, bis(methylcyclopentadienyl)magnesium, bis(ethylcyclopentadienyl)magnesium, bis(propylcyclopentadienyl)magnesium, bis(iso-propylcyclopentadienyl)magnesium, bis(n-butylcyclopentadienyl)magnesium, and bis(pentamethylcyclopentadienyl)magnesium.

5. The method of claim 1 wherein the scavenging agent is composed of a hydrocarbon moiety having two or more tertiary amine groups.

6. The method of claim 1 wherein the scavenging agent has the formula:

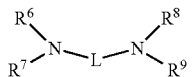
(III)

wherein: each of $R^6$, $R^7$, $R^8$, $R^9$ and $R^{10}$ are independently chosen from $(C_1\text{-}C_6)$alkyl, $(C_6\text{-}C_{10})$aryl, and $(C_1\text{-}C_6)$alkyl$(C_6\text{-}C_{10})$aryl; each of $R^6$ and $R^7$, and $R^8$ and $R^9$, may be taken together along with the nitrogen to which they are attached to form a 5- to 8-membered heterocyclic ring; $R^6$ and $R^8$ may be taken together along with the nitrogens to which they are attached to form a 5- to 8-membered heterocyclic ring; $L=(CH_2)_x(CH_2NR^{10}CH_2)_y(CH_2)_z$ or $(C_5\text{-}C_6)$cycloalkylene; x=0-10; y=0-4; and z=0 or 1; wherein x+y+z≥1.

7. The method of claim 6 wherein the scavenging agent is chosen from N,N,N',N'-tetramethylethylenediamine; N,N,N',N'-tetramethylmethylenediamine; N,N,N',N'-tetramethylpropylenediamine; N,N,N',N'-tetramethylbutylenediamine; N,N,N',N'-tetramethyl-cyclohexyldiamine; N,N,N',N'-tetraethylethylenediamine; N,N,N',N',N"-pentamethyl-diethylenetriamine; 1,1,4,7,10,10-hexamethyltriethylenetetramine; 1,2-di(pyrrolidin-1-yl)ethane; 1,2-di(piperidin-1-yl)ethane; N,N'-dimethylpiperazine; 1,4,7-trimethyl-1,4,7-triazonane; and 1,3,5-trimethyl-1,3,5-triazinane.

8. The method of claim 1 wherein the cyclopentadienyl magnesium compound is contacted with the scavenging agent in the presence of an organic solvent.

9. The method of claim 8 wherein the amount of the scavenging agent is from 0.5 to 90% by weight, based on the weight of the organic solvent.

10. The method of claim 1 wherein the step of separating the purified cyclopentadienyl magnesium compound form the scavenging agent is chosen from crystallization, sublimation, filtration and decantation.

11. The method of claim 1 wherein the purified cyclopentadienyl magnesium compound has <0.5 ppm of total detectable metals.

12. The method of claim 1 wherein the purified cyclopentadienyl magnesium compound is free of scavenging agent.

13. A method of removing metallic impurities from a cyclopentadienyl magnesium compound comprising the steps of: providing a crude bis(cyclopentadienyl)magnesium compound; contacting the crude cyclopentadienyl magnesium compound with an aprotic scavenging agent comprising two or more tertiary amine groups to purify the cyclopentadienyl magnesium compound; and separating purified cyclopentadienyl magnesium compound from the scavenging agent; wherein each cyclopentadienyl ring of the bis(cyclopentadienyl)magnesium compound may be optionally substituted with one or more $(C_1\text{-}C_4)$alkyl groups.

14. The method of claim 13 wherein the bis(cyclopentadienyl)magnesium compound is chosen from bis(cyclopentadienyl)magnesium; bis(methylcyclopentadienyl)magnesium; bis(ethylcyclopentadienyl)magnesium; bis(propylcyclopentadienyl)magnesium; bis(iso-propylcyclopentadienyl)magnesium; bis(n-butylcyclopentadienyl)magnesium; and bis(pentamethylcyclopentadienyl)magnesium.

15. The method of claim 13 wherein the scavenging agent is composed of a hydrocarbon moiety having two or more tertiary amine groups.

16. The method of claim 13 wherein the scavenging agent has the formula:

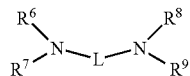
(III)

wherein: each of $R^6$, $R^7$, $R^8$, $R^9$ and $R^{10}$ are independently chosen from $(C_1\text{-}C_6)$alkyl, $(C_6\text{-}C_{10})$aryl, and $(C_1\text{-}C_6)$alkyl$(C_6\text{-}C_{10})$aryl; each of $R^6$ and $R^7$, and $R^8$ and $R^9$, may be taken together along with the nitrogen to which they are attached to form a 5- to 8-membered heterocyclic ring; $R^6$ and $R^8$ may be taken together along with the nitrogens to which they are attached to form a 5- to 8-membered heterocyclic ring; $L=(CH_2)_x(CH_2NR^{10}CH_2)_y(CH_2)_z$ or $(C_5\text{-}C_6)$cycloalkylene; x=0-10; y=0-4; and z=0 or 1; wherein x+y+z≥1.

17. The method of claim 16 wherein the scavenging agent is chosen from N,N,N',N'-tetramethylethylenediamine; N,N,N',N'-tetramethylmethylenediamine; N,N,N',N'-tetramethylpropylenediamine; N,N,N',N'-tetramethylbutylenediamine; N,N,N',N'-tetramethyl-cyclohexyldiamine; N,N,N',N'-tetraethylethylenediamine; N,N,N',N',N"-pentamethyl-diethylenetriamine; 1,1,4,7,10,10-hexamethyltriethylenetetramine; 1,2-di(pyrrolidin-1-yl)ethane; 1,2-di(piperidin-1-yl)ethane; N,N'-dimethylpiperazine; 1,4,7-trimethyl-1,4,7-triazonane; and 1,3,5-trimethyl-1,3,5-triazinane.

* * * * *